United States Patent [19]

Handt

[11] Patent Number: 4,557,727

[45] Date of Patent: * Dec. 10, 1985

[54] SPIKE EXCHANGER FOR CONTINUOUS AMBULATORY PERITONEAL DIALYSIS

[76] Inventor: Alan E. Handt, 705 Pineview, Zionsville, Ind. 46077

[ * ] Notice: The portion of the term of this patent subsequent to Sep. 20, 2000 has been disclaimed.

[21] Appl. No.: 531,822

[22] Filed: Sep. 13, 1983

Related U.S. Application Data

[63] Continuation-in-part of Ser. No. 511,555, Jul. 7, 1983, abandoned, which is a continuation-in-part of Ser. No. 371,310, Apr. 23, 1982, Pat. No. 4,405,315.

[51] Int. Cl.[4] .......................... A61M 5/14; A61J 5/00
[52] U.S. Cl. .......................................... 604/80; 604/29; 604/410; 604/411; 604/905; 222/83; 141/330
[58] Field of Search ................... 604/29, 80, 174, 178, 604/410, 411, 905; 128/346; 222/83, 89, 83.5, 129, 145; 141/330, 248

[56] References Cited

U.S. PATENT DOCUMENTS

| | | | |
|---|---|---|---|
| 4,340,052 | 7/1982 | Dennehey et al. | 604/905 |
| 4,402,691 | 9/1983 | Rosenthal et al. | 604/29 |
| 4,405,312 | 9/1983 | Gross et al. | 604/29 |
| 4,405,315 | 9/1983 | Handt | 604/411 |
| 4,432,759 | 2/1984 | Gross et al. | 604/411 |
| 4,439,193 | 3/1984 | Larkin | 604/29 |

FOREIGN PATENT DOCUMENTS

| | | | |
|---|---|---|---|
| A094318 | 8/1969 | France | 604/174 |
| WO84/00895 | 3/1984 | PCT Int'l Appl. | 604/408 |

*Primary Examiner*—Stephen C. Pellegrino
*Assistant Examiner*—Michelle N. Lester
*Attorney, Agent, or Firm*—Woodard, Weikart, Emhardt & Naughton

[57] ABSTRACT

A spike exchanger to move a spike from one peritoneal dialysis bag to another. A pair of peritoneal dialysis bags are positioned by a base having clamps for releasably closing the tubular ports of each bag. A patient connectable tube with a spike shaped end is removably mounted to a device slidably mounted on the base and guided by means of a slot and roller combination to the tubular port of either bag. Various embodiments of the slot roller mechanism guide the spike shaped end to the tubular ports. A hook shaped tool pivotally mounted upon the base is engageable to unlock a sterile clamp mounted to the spike and port of one bag. Spaced apart and integrally connected arms moveably mounted to the base receive a sterile clamp and are positionable to lockingly mount a sterile clamp to the spike and port of the other bag. A further hook shaped arm pivotally mounted to the base is moveable against a bag port to hold the port immoveably straight as it is engaged by the spike.

22 Claims, 20 Drawing Figures

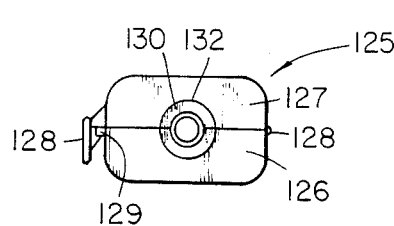
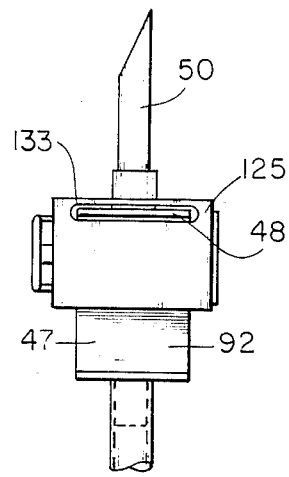
Fig.12  Fig.11
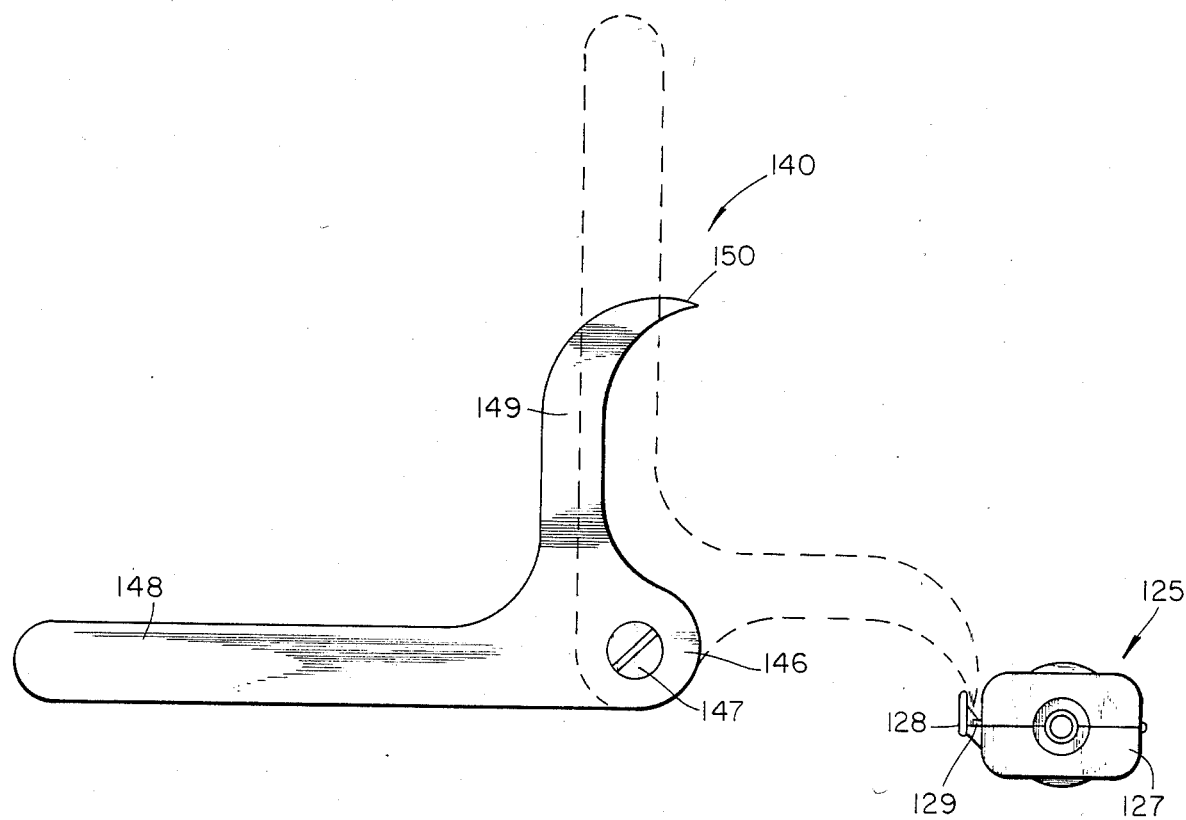
Fig.14

SPIKE EXCHANGER FOR CONTINUOUS AMBULATORY PERITONEAL DIALYSIS

BACKGROUND OF THE INVENTION

Cross-Reference to Related Applications

This application is a continuation-in-part of my copending continuation-in-part U.S. patent application, Ser. No. 511,555, filed July 7, 1983 abandoned which in turn in is continuation-in-part of my U.S. patent application, Ser. No. 371,310, filed Apr. 23, 1982 and now U.S. Pat. No. 4,405,315, issued Sept. 20, 1983.

This invention is in the field of medical devices and more specifically those devices provided to exchange a tubular spike from one bag of fluid to an adjacent bag of fluid. The device disclosed herein is particularly advantageous in changing a tubular spike from one peritoneal dialysis bag into an adjacent peritoneal dialysis bag while ensuring the connection remains sterile. Peritoneal dialysis takes advantage of the fact that the peritoneal cavity is covered by a peritoneal membrane (a thin shiny membrane covering the abdominal cavity) which can be used for transfer of body waste from the blood into the peritoneal fluid instilled into it. To perform peritoneal dialysis, a dialysis solution is placed within the abdominal cavity and left there for a period of time. During this time, molecules of waste particles from the blood diffuse across the peritoneal membrane into the fluid and the fluid is subsequently drained out and discarded with new fluid being put into the peritoneal cavity to begin the process anew.

The aforementioned process is relatively slow as compared to hemodialysis; however, with the advent of continuous peritoneal dialysis the previously described process becomes a much preferred and efficient method of treatment. In 1975, Popovich and Moncrief, described the exchange method of C.A.P.D. (continuous ambulatory peritoneal dialysis) in which two liters of fluid are placed in the abdomen and left to dwell for a period of four to eight hours. At the end of this time, the fluid is drained and two liters of new fluid is put back into the abdominal cavity. A modification of this procedure by Oreopoulos in 1977 included the use of peritoneal dialysis solution in two liter bags. The bags could then be rolled up (in the empty state) during the dwell time. These patients were amubulatory and required only one bag connection for both infusion and drainage of the fluid. C.A.P.D. has now expanded widely with over 5,000 patients in the United States now receiving this therapy for chronic renal failure. When the patient changes from the old bag to a new bag connected to the tubing inserted into the abdominal cavity, the patient must under sterile conditions remove the plastic spike from the bag that is to be discarded and sterilely place this spike into the new bag. The method now used calls for the patient to have enough strength to pull the spike out of the bag and insert it into the new bag without any deviation.

There are many advantages to C.A.P.D. For example, the patient is ambulatory, is extremely mobile and can travel virtually anyplace desired as long as the bags of fluid are taken with the patient. Further, C.A.P.D. can be performed by the patient without requiring the help of a partner. It is desirable to place a number of patients on C.A.P.D.; however, there are some limitations with the method of spike exchange now used. It has been shown that diabetics have an increased incidence of blindness and it is believed the blindness is hastened by hemodialysis. Thus, it is beneficial to place these patients on C.A.P.D. This is quite difficult because the patient cannot see well enough to make the exchange under sterile conditions and the spike becomes contaminated resulting in the patient developing peritonitis. If a blind patient or a patient with limited muscle strength or dexterity is to be placed on C.A.P.D., a partner must be used and thus decreasing the true advantages of C.A.P.D. Therefore, it would be ideal to have a mechanism by which a person who is blind, has failing eyesight, has decreased manual dexterity or decreased strength in his hands could perform the exchange of the spike by himself. Disclosed herein is such a piece of equipment allowing the change of the tubing spike from the used bag to a new bag without contamination. The exchange can be done with minimal effort with someone who has decreased vision, blindness, decreased manual dexterity or extreme weakness of the hands.

SUMMARY OF THE INVENTION

One embodiment of the present invention is a spike exchanger for continuous ambulatory peritoneal dialysis comprising a base having mounting means to releasably hold a first bag with a first port and a second bag with a second port, clamp means on the base and engageable with the first port and the second port to releasably limit fluid flow therethrough, spike holding and moving means movably mounted to the base and operable to releasably hold a spike in fluid communication with the first port and move the spike away from the first port to the second port, guide means on the base and associated with the spike holding and moving means to guide and align the spike with the second port as the spike is moved thereto, and sterile placing means moveably mounted to the base and operable to initially hold and lockingly place sterile means onto the spike and the second port to achieve a sterile environment therebetween.

Another embodiment of the present invention is a spike exchanger for continuous ambulatory peritoneal dialysis and operable with a first bag with a first port and a second bag with a second port comprising a base, clamp means on the base and engageable with the first port and the second port to releasably limit fluid flow therethrough, spike holding and moving means movably mounted to the base and operable to releasably hold a spike in fluid communication with the first port and move the spike away from the first port to the second port, guide means on the base and associated with the spike holding and moving means to guide and align the spike with the first port and the second port as the spike is respectively moved thereto, handle means pivotally mounted to the spike holding and moving means about a first axis to move the spike into and out of the first port and the second port and pivotally mounted about a second axis arranged in a direction perpendicular to the first axis to move the spike from the first port to the second port.

Yet a further embodiment of the present invention is a device for holding the conduit of a peritoneal dialysis bag comprising a base upon which the bag may be removably mounted, means movably mounted on the base and contactable with the conduit of the bag to hold the conduit immoveably straight as the conduit is operably connected.

Another embodiment of the present invention is a device for placing a sterile clamp on a peritoneal dialysis bag port comprising a base upon which a peritoneal dialysis bag may be mounted with the port thereof extending outwardly from the bag, sterile clamp holding means moveably mounted to the base and having a cavity sized to receive an opened sterile clamp and further having a channel adjacent the cavity sized to receive the clamp only in a closed condition, the clamp holding means moveable towards the port to contact the clamp against the port and force the clamp from the cavity into the channel closing the clamp onto the port.

It is an object of the present invention to provide a sterile means for changing a spike from one peritoneal dialysis bag to another without contamination.

A further object of the present invention is to provide a spike exchanger for C.A.P.D. that can be used with minimal effort by someone who has decreased vision, blindness, decreased manual dexterity or extreme weakness of the hands.

Yet another object of the present invention is to provide a new and improved apparatus for continuous ambulatory peritoneal dialysis.

In addition, it is an object of the present invention to provide a medical apparatus to change a tubular connection from a first bag for holding liquid to a second bag for holding liquid.

Yet a further object of the present invention is to provide means for holding the dialysis bag conduit port immovably straight to allow the fluid connection in an efficient and quick manner.

In addition, it is an object of the present invention to provide a tool for placing and mounting a sterile clamp onto the junction between dialysis bag conduit port and spike in fluid communication therewith.

Another object of the present invention is to provide a tool for removing the sterile clamp mounted to the junction of the dialysis bag conduit port and spike.

Related objects and advantages of the present invention will be apparent from the following description.

BRIEF DESCRIPTION OF THE DRAWINGS

FIG. 11 is an enlarged plan view of the spike and attached tube with a sterile clamp mounted to the spike.

FIG. 12 is an end view of the sterile clamp and spike shown in FIG. 11.

FIG. 14 is a cross-sectional view taken along the line 14—14 of FIG. 13 and viewed in the direction of the arrows.

DESCRIPTION OF THE PREFERRED EMBODIMENTS

Figure 1:
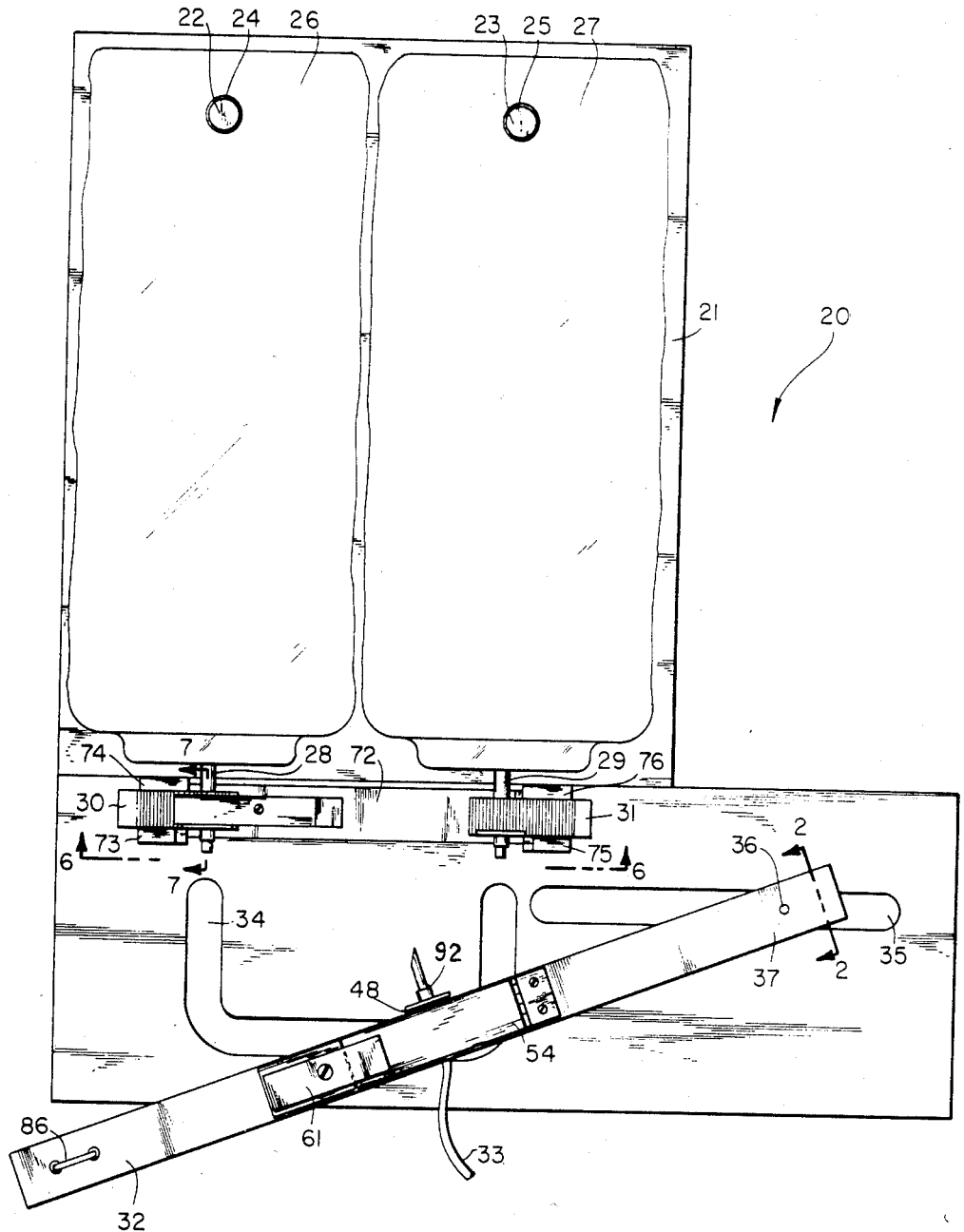
FIG. 1 is a plan view of one embodiment of the spike exchanger incorporating the present invention.

For the purposes of promoting an understanding of the principles of the invention, reference will now be made to the embodiments illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

Referring now more particularly to FIG. 1, there is shown one embodiment of the spike exchanger 20 incorporating the present invention. Spike exchanger 20 includes a base 21 having a pair of pegs 22 and 23 extending cantileveredly upward therefrom. Pegs 22 and 23 are sized to removably fit into a pair of mounting apertures 24 and 25 provided respectively on two commercially available Peritoneal Dialysis bags 26 and 27. Such bags are available, for example, from Artificial Organs Division of Travenol Laboratories, Inc., Deerfield, Ill. 60015 or Abbott Laboratories, North Chicago, Ill. 60064. The bags contain Peritoneal Dialysis solution in the amount of 2,000 mil. At the bottom end of each bag is a tubular port 28 and 29 received by a pair of clamps 30 and 31 mounted to base 21.

A slidable and pivotable lever 32 is mounted to base 21 and has means to removably secure and mount spike 92 in turn connected to spike tube 33. A C-shaped slot 34 is formed in base 21 to receive a roller mechanism mounted to lever 32 immediately beneath spike 92. A straight slot 35 is also formed in base 21 and receives a roller mechanism 36 mounted to the proximal end 37 of lever 32. The two legs of slot 34 are aligned with tubes 28 and 29 of bags 26 and 27. Thus, lever 32 may be pivoted about roller mechanism 36 and moved through slots 34 and 35 to move spike 92 toward either tube 28 or 29 to connect the spike to either bag without requiring the patient to manually hold spike 92 during the insertion or removal from either tube 28 or 29.

Figure 2:
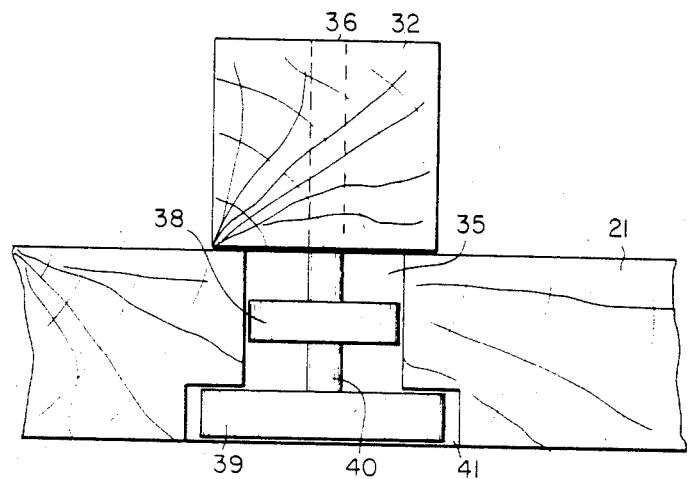
FIG. 2 is an enlarged fragmentary cross-sectional view taken along the line 2—2 of FIG. 1 and viewed in the direction of the arrows.

One end of lever 32 (FIG. 2) includes a roller mechanism 36 having a first roller 38 and a larger diameter roller 39 rotatably mounted to pin 40 fixedly mounted to lever 32. Roller 38 is slidable the length of slot 35 with a second slot 41 located immediately beneath slot 35 and of larger width to receive roller 39 and prevent the lever from moving upwardly disengaging the base. A similar roller mechanism 42 includes a pair of rollers 43 and 44 received respectively in slots 45 (FIG. 5) and 34 provided in base 21. Roller 43 is larger in diameter than roller 44 and is received in slot 45 located immediately beneath slot 34 and of larger width than slot 34 to prevent lever 32 from moving upwardly disenaging the base. Each roller 43 and 44 are rotatably mounted to pin 46 fixedly mounted to lever 32 with pin 46 being located immediately beneath spike 92.

Figure 3:
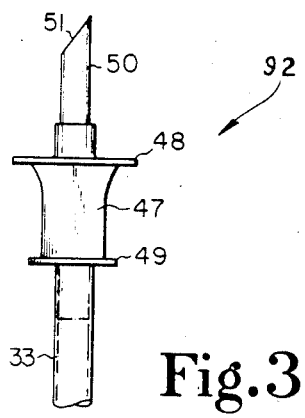
FIG. 3 is an enlarged plan view of the spike and attached tube.
Figure 4:
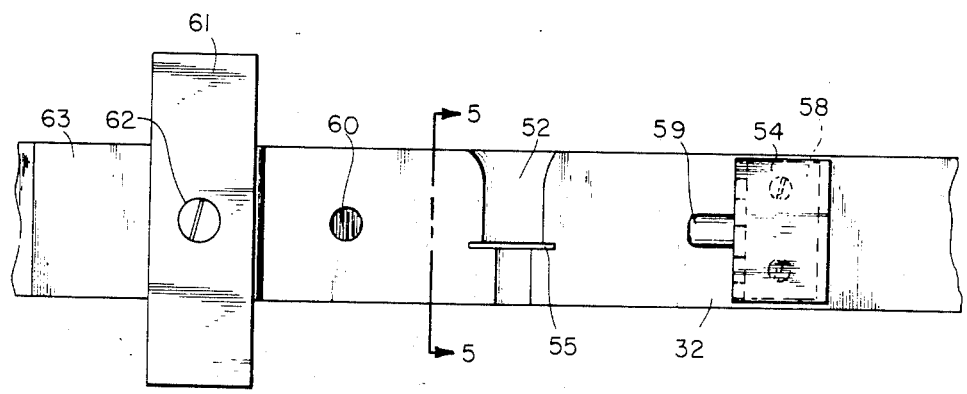
FIG. 4 is an enlarged fragmentary top view of the spike mount shown in the open position.
Figure 5:
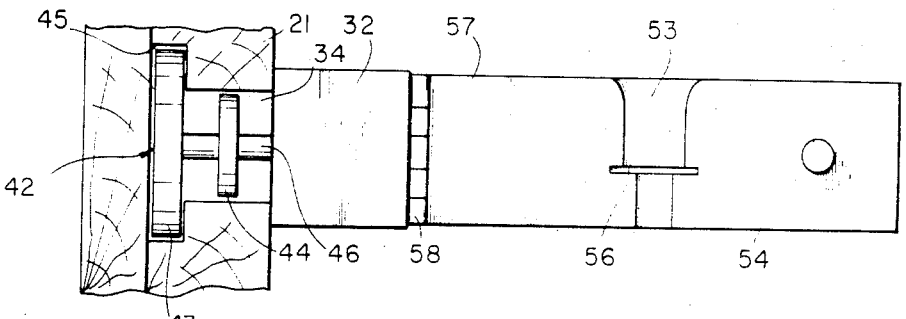
FIG. 5 is a fragmentary cross-sectional view taken along the line 5—5 of FIG. 4 and viewed in the direction of the arrows.

Spike 92 (FIG. 3) includes a main body 47 having a pair of flat plates 48 and 49 mounted to the respective ends of the main body with a passage running through the spike to allow fluid communication between hose 33 and the hollow shank 50 extending outwardly therefrom and terminating at tip 51 for piercing either tube 28 or 29 of bags 26 and 27. A complementary sized recess 52 (FIG. 4) is formed in lever 32 with a similar recess 53 formed in mounting block 54 (FIG. 5). Mounting block 54 is shown in the upward or open position with the spike removed in FIGS. 4 and 5 to illustrate recesses 52 and 53. Recessess 52 and 53 have respectively slots 55 and 56 formed therein to mountingly receive plate 49 (FIG. 3) of the spike. The second plate 48 fits outwardly of block 54 (FIG. 1) when the spike is mounted in recesses 52 and 53 and block 54 is pivoted downward to the closed position. End 57 (FIG. 5) of block 54 is hingedly mounted by a conventional hinge 58 to lever 32. An alignment pin 59 is provided in the distal end of block 54 and is received by aperture 60 in lever 32 when the block is in the downward or closed position. Once mounting block 54 is pivoted to the downward or closed position, a locking member 61 is moved to a position outwardly of and against the distal end of mounting block 54 preventing relative motion between mounting block 54 and lever 32. Locking member 61 is pivotally mounted by a conventional fastener 62 in turn secured to member 63 fixedly mounted to lever 32.

Figure 6:
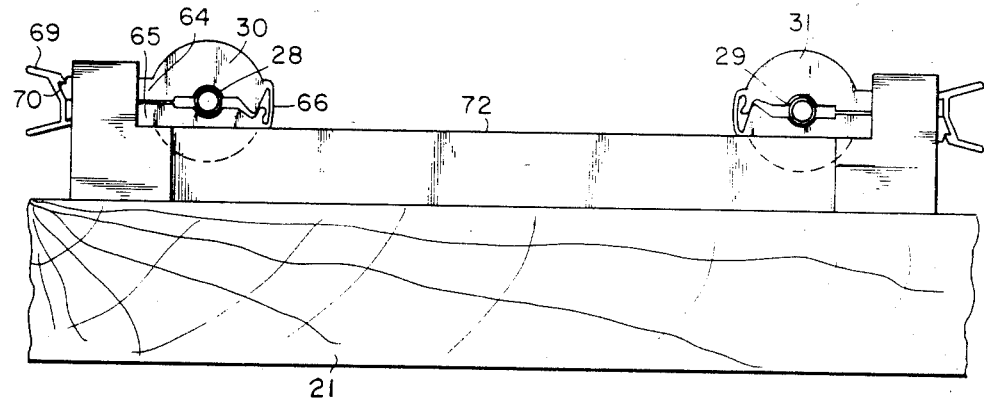
FIG. 6 is an enlarged fragmentary cross-sectional view taken along the line 6—6 of FIG. 1 and viewed in the direction of the arrows.
Figure 7:
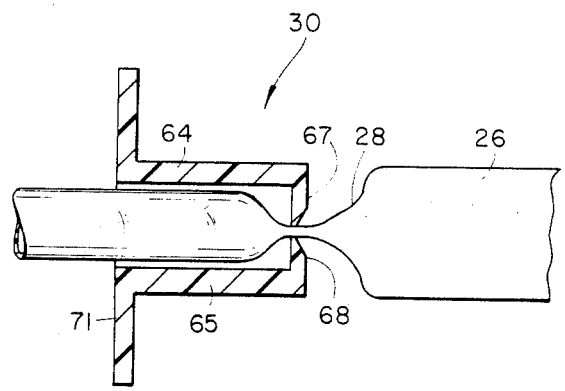
FIG. 7 is an enlarged fragmentary cross-sectional view taken along the line 7—7 of FIG. 1 and viewed in the direction of the arrows.

Tube clamp 30 will now be described it being understood that a similar description applies to tube clamp 31. Clamp 30 (FIG. 6) includes an upper clamp half 64 and a lower clamp half 65 hingedly connected together by means of a plastic hinge 66. Each half portion 64 and 65 have mating ridges 67 and 68 (FIG. 7) which meet and squeeze shut conduit 28 of bag 26 when the top half portion 64 is pivoted to the downward locked position. A bendable locking handle 69 is integrally connected to bottom half portion 65 (FIG. 6) and lockingly and removably engages ridge 70 provided on the distal end of the top half portion 64. To remove conduit 28 from clamp 30, handle 69 may be pivoted downwardly to the left as viewed in FIG. 6 disengaging ridge 70 and allowing top half portion 64 to be pivoted upwardly around hinge 66. The bottom half portion 65 has a semi-circular plate 71 formed thereon which is removably received in a complementary sized slot provided in inlet port holder 72 (FIG. 6). Holder 72 (FIG. 1) consists of an elongated member extending across base 21 and fixedly secured thereto with each end of holder 72 having a pair of ears 73-74 and 75-76 to receive respectively clamps 30 and 31 positioned therebetween. Ears 73 and 74 prevent clamp 30 from moving parallel to base 21; however, clamp 30 along with bag 26 may be picked upwardly and removed from base 21. Ears 75 and 76 likewise prevent motion of clamp 31 in a direction parallel to base 21 with the top half portion of clamp 31 being pivoted upwardly to allow conduit 29 to be removed from the clamp and bag 27 to be removed from base 21. As will be apparent from a later description herein, it is unnecessary to remove clamp 31 from base 21 and as a result, the bottom half portion of clamp 31 is fixedly secured by a bolt or other conventional fastening device to base 21.

Figure 8:
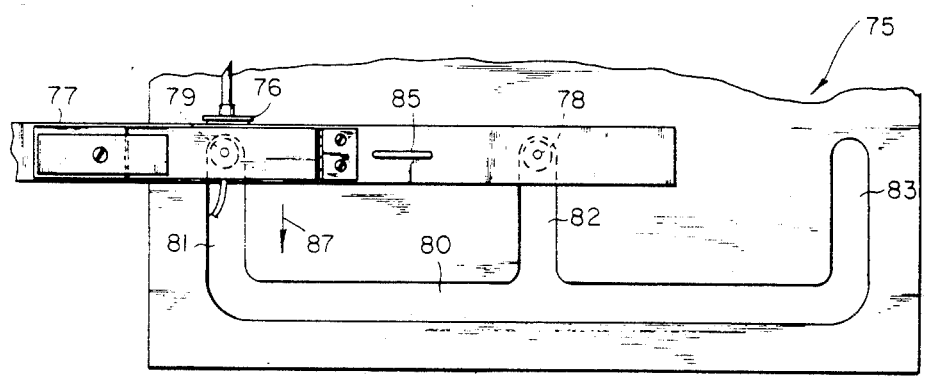
FIG. 8 is a fragmentary plan view of an alternate embodiment of the spike exchanger.

An alternate embodiment of the spike exchanger is partially depicted in FIG. 8. Exchanger 75 is identical to exchanger 20 with the exception of the design of the slot provided in the base for slidably receiving the spike mounting lever. Spike 76 is removably mounted to lever 77 in the same manner as the mounting of spike 92 to lever 32. A roller mechanism 78 identical to roller mechanism 36 is mounted to one end of lever 77 with a second roller mechanism 79 identical to roller mechanism 42 being mounted to lever 77 immediately beneath spike 76. When the spike is engaged with conduit 28 of the left bag 26, roller mechanisms 79 and 78 are positioned respectively in legs 81 and 82 of slot 80 whereas when spike 76 is engaged with conduit 29 of bag 27, roller mechanisms 79 and 78 are positioned respectively in legs 82 and 83 of slot 80. Handle 85 is mounted to lever 77 between roller mechanism 78 and 79 in contrast with the mounting of handle 86 which is positioned at one end of lever 32. The handles may take any form including a peg shape. To remove spike 76 from the left bag 26 and to engage the spike with the right bag 27, handle 85 is grasped and lever 77 is pulled in the direction of arrow 87 and then moved to the right until roller mechanisms 79 and 78 are positioned in legs 82 and 83 of slot 80 with the lever then being pushed in a direction opposite arrow 87. Legs 81 and 82 of the slot are aligned respectively with conduits 28 and 29 of bags 26 and 27.

Figure 9:
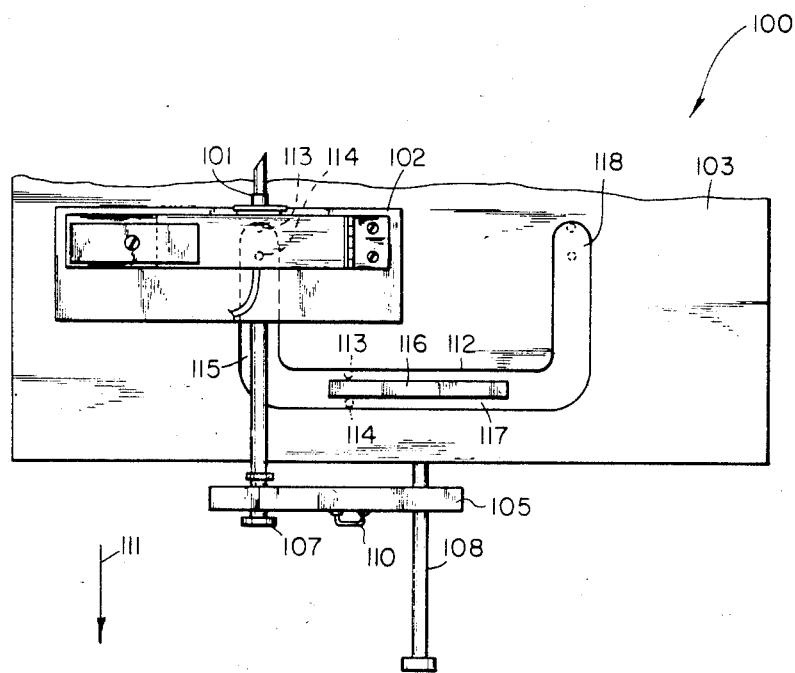
FIG. 9 is a fragmentary plan view of a further embodiment of the spike exchanger.
Figure 10:
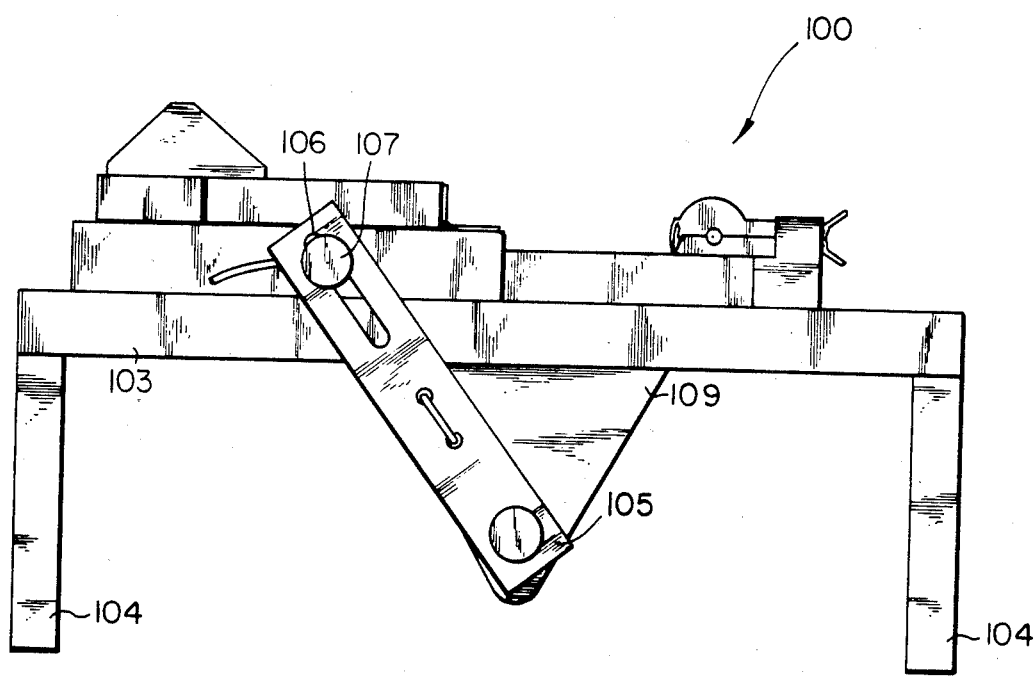
FIG. 10 is an end view of the spike exchanger shown in FIG. 9.

A further embodiment of the spike exchanger is shown in FIGS. 9 and 10. Spike exchanger 100 is identical with spike exchanger 20 with the exception of the design of the slot and the associated mounting lever. Spike 101 is removably mounted to block 102 in a manner identical to the mounting of spike 92 to lever 32. Block 102 is slidably mounted to base 103 which in turn may be supported upon frame 104 (FIG. 10). Pivotally mounted to and beneath base 103 is arm 105 having a slot 106 formed in the top end thereof to slidably receive a double headed rod 107 fixedly mounted to block 102. Arm 105 is slidably mounted to a headed rod 108 fixedly mounted by bracket 109 to base 103. By grasping handle 110 and moving arm 105 in the direction of arrow 111, the arm will pull headed rod 107, block 102 and spike 101 disengaging the spike from the left bag 26. Arm 105 may then be pivoted in a clockwise direction as viewed in FIG. 10 until the spike is aligned with conduit 29 of the right bag 27 with arm 105 then being forced in a reverse direction opposite of arrow 111 until the spike engages conduit 29. Slot 106 is provided to enable rod 107 to move through the slot as arm 105 is pivoted from the left to the right and back. Slot 112 is provided in base 103 and is C-shaped in configuration to slidably receive a pair of roller mechanisms 113 and 114 fixedly mounted to and beneath block 102 with each roller mechanism 113 and 114 being identical in construction to roller mechanism 42. The roller mechanisms are aligned with spike 101 in the direction of leg 115 of slot 112. Thus, when the handle 110 is moved to the most outward position in the direction of arrow 111, and the lever pivoted to the right, roller mechanisms 113 and 114 will span on opposite sides ridge 116 extending the length of the portion 117 of slot 112 connecting slot legs 115 and 118 together. Ridge 116 provides for lateral stability as the spike is moved from one bag to another bag. Roller mechanisms 113 and 114 are shown in phantom in portion 117 and slot 118 to illustrate the positioning thereof as spike 101 is moved. Likewise, when the spike is positioned immediately above leg 118 of the slot, the two roller mechanisms will be aligned with conduit 29 in the direction of the length of leg 118. The remaining structure of spike exchanger 100 is identical to that previously described for the other spike exchangers and includes a pair of clamps for removably receiving the bag tubes.

The spike exchanger includes a mechanism to mobilize both the old and new bag of fluid using clamps which are placed over the tubular ports. The spike is placed in a clamp on a moveable portion of the device with the moveable portion then being shifted from the old bag to the new bag, thereby swiftly and sterilely removing the spike from the old bag and placing it in the new bag. To begin, the peritoneal dialysis solution in a first bag is drained into the patient with the empty first bag then being rolled up and carried by the patient. Upon completion of the dwell time, the first empty bag is unrolled with the solution within the patient being allowed to drain back into the first bag. With the embodiment depicted in FIG. 1, the first bag is shown as bag 26. As bag 26 is mounted to base 21, spike exchanger 92 is mounted to lever 32 and clamp 30 is moved to the closed position. Lever 32 is then grasped and pulled outwardly and moved to the right disengaging spike 92 relative to conduit 28. Lever 32 is then moved inwardly to engage spike 92 with conduit 29. Clamp 31 is then opened allowing the contents of bag 27 to drain into the patient. Once bag 27 is empty, the bag may be rolled up along with spike 32 and carried by the patient during the dwell time after which the process is repeated. During the dwell time, bag 26 is emptied and a new bag with fresh peritoneal dialysis solution 15 is mounted to the right side of base 21. The same procedure applies to the embodiment depicted in the other drawings. To ensure a sterile environment between the spike and tube conduit, suitable sterile wrappings, gauze or similar material should be positioned around spike 92 and the mating tubular port 28 or 29 while interconnected. Plate 48 of spike 92 is positioned outwardly and is spaced apart from lever 32 to facilitate the mounting of a clam shaped shell onto the spike (FIG. 11) with the shell containing therein sterile materials providing a sterile environment.

Pegs 22 and 23 provide mounting means to releasably hold the two bags having tubular ports. Further, clamps 30 and 31 provide a clamp means on base 21 engageable with the pair of tubular ports to releasably limit fluid flow therethrough. Bar 32 along with locking member 54 provide a spike holding and moving means movably mounted to the base and operable to releasably hold spike 92 in fluid communication with tubular port 28 and to move spike 92 away from tubular port 28 to the second tubular port 29. The slots provide a guide means on the base and associated with bar 32 to guide and align the spike with tubular port 29 as the spike is moved thereto. The slot provides a track having a pair of interconnected parallel legs extending away from the tubular ports. The roller mechanisms such as mechanism 42 provide a bearing surface which is slidably moveable over the slot legs to align the spike with the tubular ports. Recesses 52 and 53 provide a recess means to hold in position the spike in line with the tubular ports when the bearing surface is positioned in the respective legs of the slot. Spike 92 is mounted to the end of a patient connectable tube 33 with the spike end fittable into either tubular port 28 or 29. Ears 73-74 and 75-76 along with the slots provided in member 72 receiving the disk shaped bottom half portion 65 of clamp 30 and the disk shaped bottom portion of clamp 31 provide an alignment means to limit relative movement between the clamps and base 21 and further align the tubular ports with the spike.

Many advantages of the present invention will be apparent upon use of the device. Previously, the manual removal of the spike from one bag and manual insertion into the inlet port of a new bag was accomplished with a high risk of contamination. Such risk of contamination is considerably reduced by utilizing the device disclosed herein. Further, my device allows for the procedure to be accomplished by someone who is handicapped with blindness or by someone who is handicapped by having decreased manual dexterity, perhaps secondary to crippling arthritis or muscle weakness. Likewise, the procedure may be accomplished by a patient who is handicapped by being unable to learn the proper manual technique or by someone who is handicapped by having only one upper extremity. The device disclosed herein will decrease the number of episodes of peritonitis and therefore will become very cost effective.

Spike 92 is shown in FIG. 11 having a sterile clamp 125 removably mounted thereto. Clamp 125 was designed by a person other than the present inventor and is commercially available. The clamp includes a pair of mating shells 126 and 127 connected together by means of a living hinge 128 with the opposite ends having a mating latch 128 and projection 129. The shells are hollow having a sponge-like material 130 positioned therein to hold a sterile scrub solution such as Betadine. The sponge material 130 is sufficiently resilient to allow the spike shaped end 50 and the conduit port 131 (FIG. 13) of bag 27 to extend therethrough. The shells are produced from a plastic material and have aligned apertures to form a circular hole 132 (FIG. 12) facing the conduit port of the dialysis bag. The opposite sides of the shells have aligned apertures to form a rectangular opening to allow the main body 47 of the spike to extend therethrough. In addition, both shells have a slot 133 (FIG. 11) extending therethrough to allow the plate shaped end 48 of main body 47 to extend outwardly from the shells. Slots 133 are positioned adjacent the side of the shells through which the spike main body extends.

Figure 13:
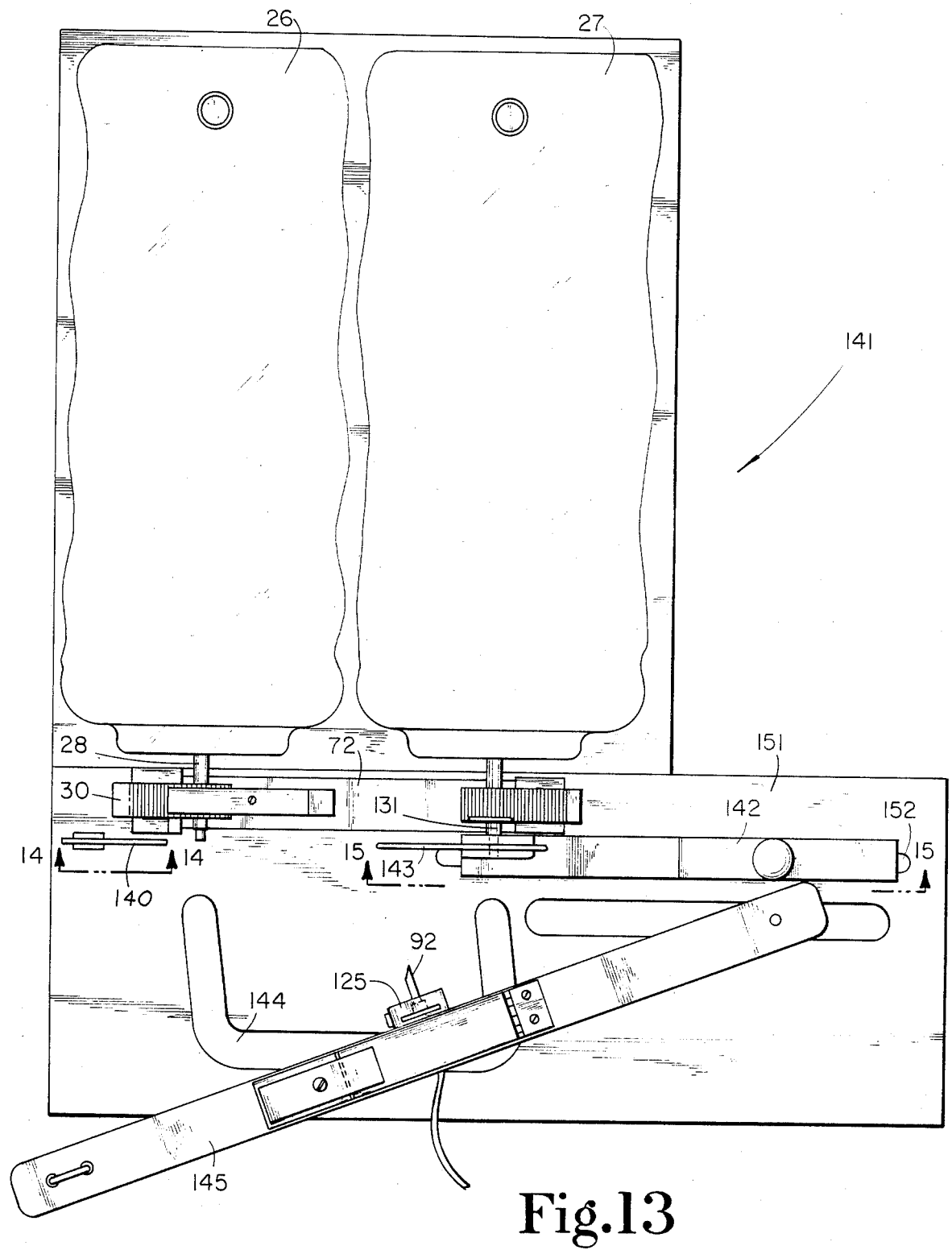
FIG. 13 is a plan view of a variation of the one embodiment of the spike exchanger incorporating means for mounting and unmounting the sterile clamp to the spike and additional means for holding the bag conduit port straight for spike insertion.

It is known to mount the sterile clamp to the junction between the spike and conduit port; however, many patients have difficulty in both mounting and removing the sterile clamp. Latch 128 is integrally connected to shell 127 and has an aperture through which projection 129 extends. In order to remove the clamp, the patient must locate latch 128 and then slightly bend the latch to disengage projection 129. The latch is relatively small and thus, considerable difficulty may be encountered by the patient in removing the clamp. Thus, a clamp unlocking tool 140 (FIG. 13) is provided immediately adjacent the conduit port 28 of bag 26. The spike exchanger 141 shown in FIG. 13 is identical to the spike exchanger 20 with the exception that additional tools are provided on spike exchanger 141. The spike exchanger shown in FIG. 13 includes a clamp unlocking tool 140, a clamp placing and locking tool 142 and a conduit port holding tool 143. In addition, the legs of slot 144 provided in the base of the spike exchanger do not extend parallel to the bag conduit ports but extend angularly therefrom to allow for the pivoting motion of the spike exchanger bar 145 as the bar is moved towards or away from the bag conduit ports.

Tool 140 (FIG. 14) includes a main body 146 pivotally mounted by conventional fastening device 147 to port holder 72 previously described and mounted to the base of the spike exchanger. Main body 146 has a lever arm 148 integrally connected to a hook shaped arm 149 in turn having a pointed distal end 150 to move downwardly as shown by the dashed line as lever 148 is pivoted upwardly thereby engaging the upward turned latch 128 of the bottom shell 127 forcing the latch away from projection 129 of the top shell of clamp 25 unlocking the clamp and allowing the patient to remove the clamp from the spike and conduit port.

The base 151 of the spike exchanger is provided with a slot 152 (FIG. 13) which extends perpendicular to the conduit port 131 of dialysis bag 27. Tool 142 is slidably mounted to base 151 and may be moved to place and lock the sterile clamp onto spike 92 and the conduit port 131.

Figure 15:
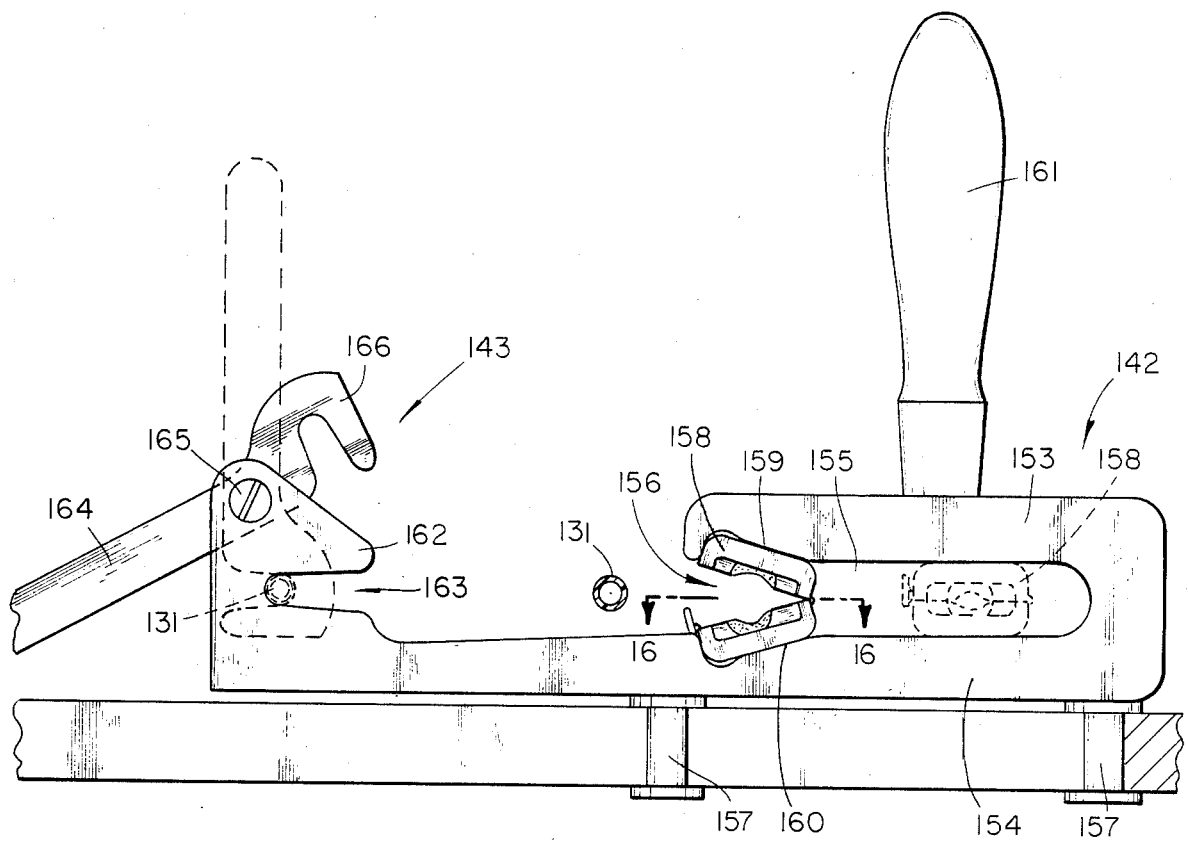
FIG. 15 is a fragmentary cross-sectional view taken along the line 15—15 of FIG. 13 and viewed in the direction of the arrows.
Figure 16:
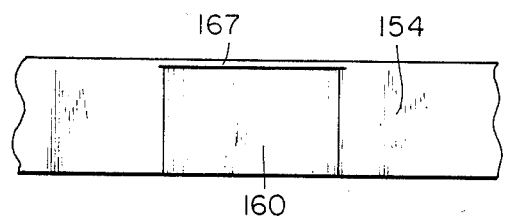
FIG. 16 is a fragmentary cross-sectional view taken along the line 16—16 of FIG. 15 and viewed in the direction of the arrows.

Tool 142 (FIG. 15) includes a pair of spaced apart arms 153 and 154 integrally connected together forming a slot 155 opening into a mount 156. A vertical side wall 167 (FIG. 16) is integrally connected to arm 154 and extends upwardly from recess 160 to provide a backstop preventing clamp 158 from exiting from the back of the tool as the clamp is initially inserted into the mouth from the front. Arm 154 includes a plurality of rollers 157 extending through slot 152 locking the tool to base 151 but allowing the tool to slide in a direction perpendicular to the conduit port 131. Slot 155 is sized to receive a closed and locked clamp 158 identical to the clamp shown in FIG. 12. Mouth 156 on the other hand is sized to receive clamp 158 in an opened, unlocked position. Arm 153 includes a downwardly opening recess 159 whereas arm 154 includes an upwardly opening recess 160 aligned with recess 159. Both recess 159 and 160 are complementary in shape to receive the top and bottom half portions of clamp 158. A handle 161 is fixedly mounted and extends upwardly from arm 153.

A conduit port holding tool 143 is mounted to arm 154 opposite of tool 142. A double walled, hook shaped bracket 162 is fixedly secured to arm 154 and extends upwardly therefrom forming a slot 163 into which conduit 131 may slide. A lever 164 is pivotally mounted by a conventional fastening device 165 between the double walls of bracket 162 and has a hook shaped end 166 which may be pivoted donwardly as shown by the dashed lines so that the recess formed by end 166 opens in a direction opposite of slot 163 thereby holding conduit 131 immovably straight between the double walls of bracket 162 and the hook shaped end 166.

The operation of spike exchanger 141 is identical to the operation of spike exchanger 20 previously described with the exception that the three aforementioned tools are incorporated into the operation. Upon completion of the dwell time, the first bag 26 has spike 92 mounted to the conduit port. Clamp 30 is moved to the closed position and lever 148 is pivoted until the pointed end 150 engages and unlocks projection 128 of clamp 125. The clamp is then removed and the lever 145 is pulled outwardly disengaging spike 92 from conduit port 28. Spike 92 is then aligned with conduit port 131 and tool 143 is moved rightward in slot 152 until conduit port 131 extends through slot 163. Lever 164 (FIG. 15) is then pivoted until the hook shaped end 166 engages the conduit port holding the port in an immovable straight position against bracket 162. Spike 92 is then inserted into conduit port 131. Lever 164 is then pivoted in an opposite direction and handle 161 is grasped moving tool 142 to the left until the spike and conduit enter mouth 156 engaging the top and bottom halves of clamp 158. Tool 142 is moved further to the left as viewed in FIG. 15 thereby forcing clamp 158 into slot 155 and locking the top and bottom halves of the clamp together and onto the spike and conduit port 131.

Figure 17:
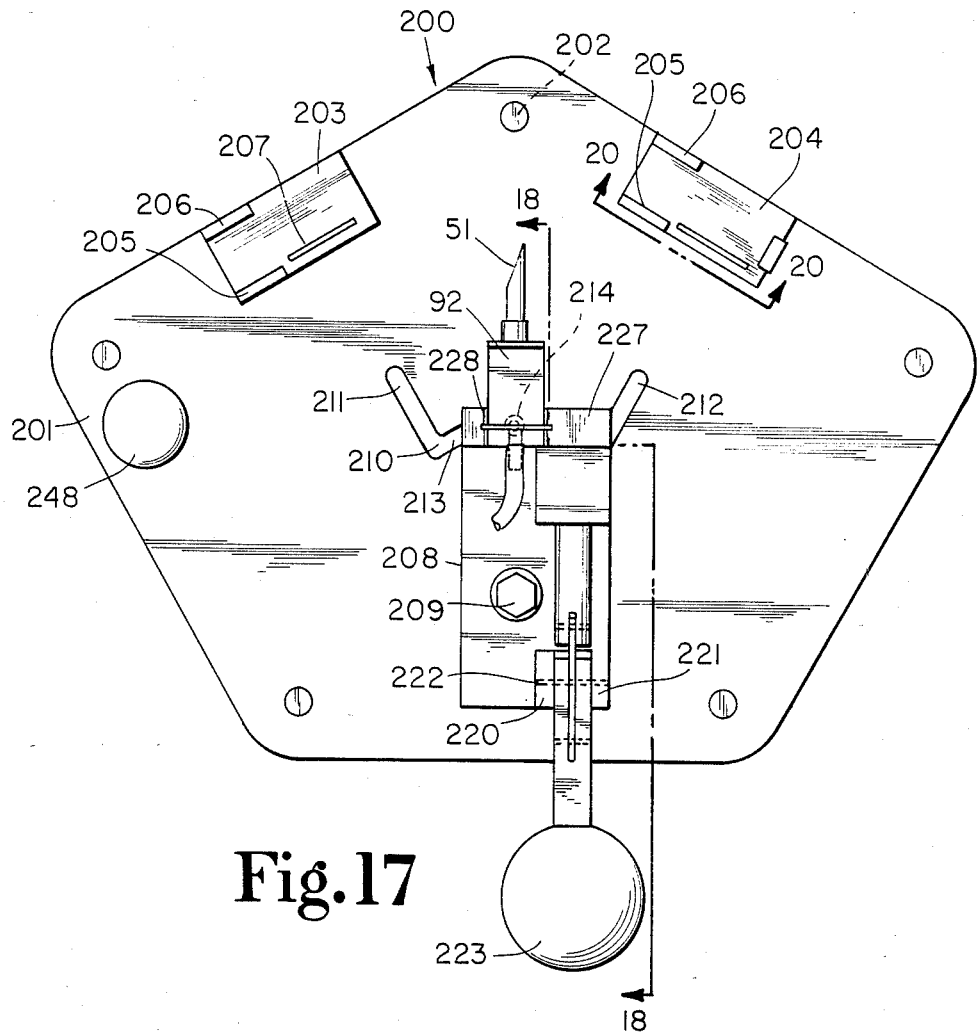
FIG. 17 is a plan view of the preferred embodiment of the spike exchanger incorporating the present invention.
Figure 18:
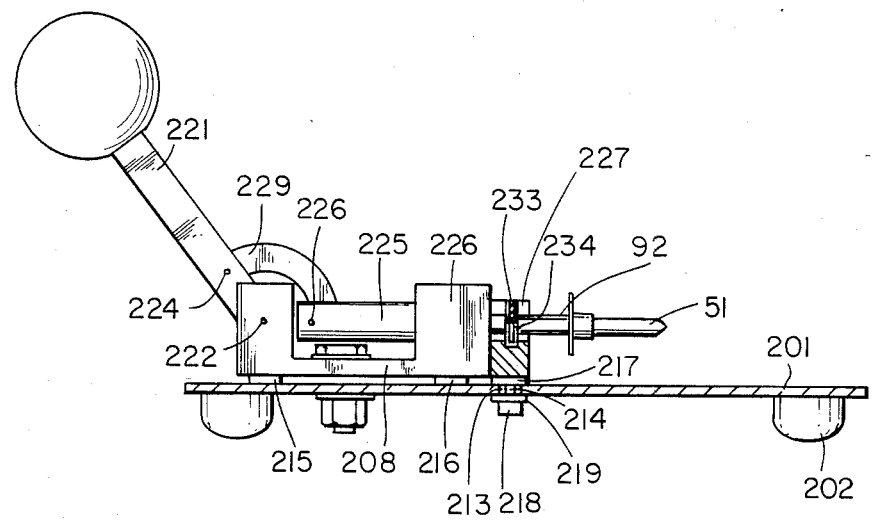
FIG. 18 is a cross-sectional view taken along the line 18—18 of FIG. 7 and viewed in the direction of the arrows.

The preferred embodiment of the spike exchanger is shown in FIGS. 17 and 18. Spike exchanger 200 includes a base plate 201 mounted atop a plurality of legs 202 depending therefrom. A pair of nesting blocks 203 and 204 are fixedly mounted atop plate 201 and are operable to hold clamps 30 and 31 previously described. Each block 203 and 204 include a pair of ears 205 and 206 along with a slot 207 to limit movement of the clamp. Ears 205 and 206 extend upwardly externally against the clamp whereas slot 207 receives the flange extending downwardly from the clamp. The clamps have been omitted from FIG. 17 to more clearly illustrate the embodiment. Ears 205 and 206 are located on the left side of each block 203 and 204 as viewed in FIG. 17.

A toggle block 208 is pivotally mounted by a conventional fastening device 209 to the top of plate 201. Fastener 209 extends through the plate and may take the form of a hexagonally shaped bolt and nut combination. A guide slot 210 extends completely through plate 201 and is composed of a pair of legs 211 and 212 leading into an arcuate shaped slot 213. Slots 211 and 212 are arranged perpendicularly with respect to blocks 203 and 204 and are aligned with the port of each bag respectively mounted by clamps 30 and 31 to blocks 203 and 204. Arcuate shaped slot 213 is defined by a single radius extending from the centerline of fastener 209 to the slot. A guide pin 214 (FIG. 18) extends downwardly immediately beneath spike 92, aligned with tip 51 and from spike holder 227 attached to block 208.

A pair of flexible washers 215 and 216 are mounted to and beneath block 208 and ride upon the top surface of plate 201 to facilitate the sliding motion of the block across the plate. In addition, a pair of washers 217 and 219 are mounted to pin 214 on the opposite sides of plate 201. A headed fastener 218 is threaded into the bottom end of pin 214 securing washer 219 therebetween. The opposite end of pin 214 is fixedly mounted to and beneath spike holder 227.

Block 208 includes a pair of upstanding ears 220 and 221 having a pivot arm 221 pivotally mounted thereto by pivot pin 222 extending through both ears and the bottom end of pivot arm 221. The opposite or top end of the pivot arm is provided with a ball handle 223 fixedly secured thereon. An arcuate shaped link 229 has one end pivotally attached to arm 221 by fastener 224 with the opposite or bottom end of the link attached to the distal end of piston rod 225 by pin 226. Piston rod 225 is slidably and reciprocatively mounted in boss 226 of block 208. The opposite end of piston rod 225 is fixedly mounted to spike holder 227 which is slidable across the top surface of plate 201. Suitable bearings are provided in boss 226 to slidably receive piston rod 225.

Figure 19:
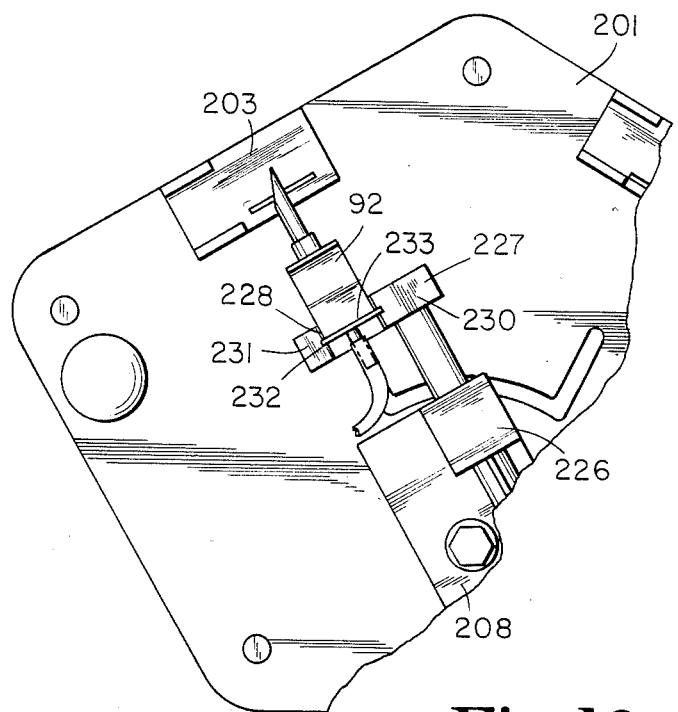
FIG. 19 is a fragmentary plan view of the spike exchanger with the spike in the engaging position.
Figure 20:
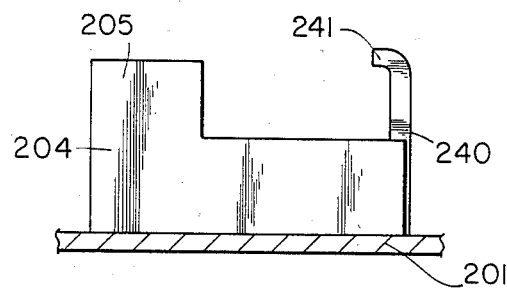
FIG. 20 is an enlarged cross-sectional view taken along the line 20—20 of FIG. 17 and viewed in the direction of the arrows.

Spike holder 227 (FIG. 17) includes a recess to removably receive one end of the main body of spike 92. Tip 51 extends outwardly away from spike holder 227 toward either bag port mounted to nesting blocks 203 and 204. In the fully retracted position, arm 221 is in the rearward position (FIG. 18) with the tip 51 of the spike not engaging either port. Once block 208 is pivoted about the centerline axis of fastener 209 (FIG. 17) and spike 92 is aligned with either slot 211 or 212, then the handled arm may be pivoted upward and toward the port of the bag thereby forcing piston rod 225 through boss 226 and causing spike holder 227 to move apart from boss 226 is depicted in FIG. 19.

Spike holder 227 includes a pair of upstanding arms 230 and 231 defining recess 228 with each having mutually opposed and aligned slots 232 to receive the plate configured flange 233 attached to the main body of spike 92. A stop surface or pin 234 extends across recess 232 (FIG. 18) on the opposite sides of the slot to engage a ledge on plate 233 thereby properly positioning spike 92 with respect to plate 201 and the bag ports mounted to blocks 203 and 204.

The operation of the embodiments shown in FIG. 17 is identical to that previously described in that spike 92 is caused to enter the port of the bag mounted to block 203 by simply aligning spike 92 with slot 211 and then pivoting ball 223 upwardly. To disengage the spike from the bag port mounted to block 203, ball 223 is pivoted rearwardly and block 208 is pivoted in a clockwise direction as viewed in FIG. 17 until spike 92 is aligned with slot 212. Ball handle 223 is then pivoted upwardly again until the tip of the spike pierces the bag port mounted atop nesting block 204. A handle rod 248 is cantileveredly mounted to plate 201 and extends upwardly therefrom to allow the user to grasp with one hand while handled arm 223 is pivoted upwardly towards either bag and pivoted about the centerline of fastener 209.

In order to keep the port of the second bag mounted to nesting block 204 straight during the piercing step by the spike 92, there is provided an upwardly extending finger 240 fixedly mounted to one end of block 204. The top end 241 of finger 240 curves inwardly providing a limiting surface against which the bag port is positioned thereby preventing the port from moving outwardly or upwardly away from the block as the spike enters the port.

The handle arm 221 is pivoted about a horizontal axis and in conjunction with toggle block 208 about a vertical axis. Thus, the handle arm provides a handle means pivotally mounted about a first or horizontal axis to move the spike in and out of the bag ports and also about a second axis perpendicular to the first axis to move the spike from the first bag port to the second bag port. The spike holder 227 or slide has a pin 214 positioned at all times along a line intersecting and perpendicularly arranged with respect to the second axis extending through fastener 209.

While the invention has been illustrated and described in detail in the drawings and foregoing description, the same is to be considered as illustrative and not restrictive in character, it being understood that only the preferred embodiments have been shown and described and that all changes and modifications that come within the spirit of the invention are desired to be protected.

The invention claimed is:

1. A spike exchanger for continuous ambulatory peritoneal dialysis and operable with a first bag with a first port and a second bag with a second port comprising:
    a base;
    clamp means on said base and engageable with said first port and said second portion to releasably limit fluid flow therethrough;
    spike holding and moving means movably mounted to said base and operable to releasably hold a spike in fluid communication with said first port and move said spike away from said first port to said second port;
    guide means on said base and associated with said spike holding and moving means to guide and align said spike with said second port as said spike is moved thereto; and,
    sterile placing means moveably mounted to said base and operable to initially hold and lockingly place sterile means onto said spike and said second port to achieve a sterile environment therebetween.

2. The spike exchanger of claim 1 and further comprising first sterile means mountable to said spike and said first port for providing a sterile environment therebetween.

3. The spike exchanger of claim 2 and further comprising second sterile means mountable to said spike and said second port providing a sterile environment therebetween; and,
    unlocking means mounted on said base adjacent said first port and moveable against said first sterile means to unlock said first sterile means from said spike.

4. The spike exchanger of claim 3 wherein said unlocking means includes a hook shaped member moveably mounted on said base, said hook shaped member having a pointed end, engageable with said first sterile means to open same.

5. The spike exchanger of claim 4 wherein said placing means includes a tool slidably mounted to said base in a direction perpendicular to said second port with said tool including a pair of spaced apart arms forming a channel and a mouth in communication therewith, said channel sized to receive said second sterile means in a closed locked position on said spike and said mouth sized to receive said second sterile means in an open position to be mounted on said spike, said tool slidable to force said mouth with second sterile means therein past said spike moving said second sterile means out of said mouth into said channel closing and mounting said second sterile means onto said spike.

6. The spike exchanger of claim 5 wherein said tool includes stop means in said mouth limiting movement of said second sterile means in a direction other than the direction of movement of said tool.

7. The spike exchanger of claim 1 and further comprising port holding means mounted on said base and engageable with said second port and operable to hold said second port straight as said spike enters said second port.

8. A spike exchanger for continous ambulatory peritoneal dialysis comprising:
    a base having clamping means to releasably hold a first port of a first bag and a second port of a second bag;

spike holding and moving means movably mounted to said base and operable to releasably hold a spike in fluid communication with said first port and move said spike away from said first port to said second port;

guide means on said base and associated with said spike holding and moving means to guide and align said spike with said second port as said spike is moved thereto; and, port holding means mounted on said base and engageable with said second port and operable to hold said second port straight as said spike enters said second port.

9. The spike exchanger of claim 8 and further comprising first sterile means mountable to said spike and said first port being operable to provide a sterile environment therebetween;

second sterile means mountable to said spike and said second port being operable to provide a sterile environment therebetween;

placing means moveably mounted to said base and engageable with said second sterile means being operable to place said second sterile means lockingly onto said spike in said second port; and wherein:

said port holding means is mounted with said placing means on said base and is slidable therewith.

10. The spike exchanger of claim 9 wherein said placing means includes a tool slidably mounted to said base in a direction perpendicular to said second port with said tool including a pair of spaced apart arms forming a channel and a mouth in communication therewith, said channel sized to receive said second sterile means in a closed locked position on said spike and said mouth sized to receive said second sterile means in an open position to be mounted on said spike, said tool slidable to force said mouth with second sterile means therein past said spike moving said second sterile means of said mouth into said channel closing and mounting said second sterile means onto said spike.

11. The spike exchanger of claim 10 wherein said tool includes stop means in said mouth limiting movement of said second sterile means in a direction other than the direction of movement of said tool.

12. The spike exchanger of claim 8 and further comprising:

first sterile means mountable to said spike and said first port for providing a sterile environment therebetween;

second sterile means mountable to said spike and second port for providing a sterile environment therebetween; and, unlocking means mounted on said base adjacent said first port and moveable against said first sterile means to unlock said first sterile means from said spike.

13. The spike exchanger of claim 12 wherein said unlocking means includes a hook shaped member moveably mounted on said base with a pointed end engageable with said first sterile means to open same.

14. A spike exchanger for continuous ambulatory peritoneal dialysis and operable with a first bag with a first port and a second bag with a second port comprising:

a base;

clamp means on said base and engageable with said first port and said second port to releasably limit fluid flow therethrough;

spike holding and moving means movably mounted to said base and operable to releasably hold a spike in fluid communication with said first port and move said spike away from said first port to said second port;

guide means on said base and associated with said spike holding and moving means to guide and align said spike with said first port and said second port as said spike is respectively moved thereto;

handle means pivotally mounted to said spike holding and moving means about a first axis to move said spike into and out of said first port and said second port and pivotally mounted about a second axis arranged in a direction perpendicular to said first axis to move said spike from said first port to said second port.

15. The spike exchanger of claim 14 wherein said guide means includes a slot having a pair of legs extending in the direction of respectively said first port and said second port and an arcuate slot joining said legs together and defined by a radius exttending from said second axis.

16. The spike exchanger of claim 15 wherein said spike holding and moving means includes a block pivotally mounted to said base about said second axis and a slide reciprocatively mounted to said block and moveable along the length of each leg of said slot.

17. The spike exchanger of claim 16 wherein said spike holding and moving means includes a piston rod slidably mounted to said block and connected to and between said slide and said handle means.

18. The spike exchanger of claim 17 wherein said handle means includes an arm having a bottom end pivotally mounted to said block and linkedly joined to an end of said piston rod.

19. The spike exchanger of claim 18 wherein said slide includes means extending into said slot and engageable with said plate being mounted beneath said slide and positioned at all times along a line intersecting and perpendicularly arranged with respect to said second axis.

20. A device for placing a sterile clamp on a peritoneal dialysis bag port comprising:

a base upon which a peritoneal dialysis bag may be mounted with the port thereof extending outwardly from said bag;

sterile clamp holding means moveably mounted to said base and having a cavity sized to receive an opened sterile clamp and further having a channel adjacent said cavity sized to receive said clamp only in a closed condition, said clamp holding means moveable towards said port to contact said clamp against said port and force said clamp from said cavity into said channel closing said clamp onto said port.

21. The device of claim 20 wherein said sterile clamp holding means includes a pair of spaced apart arms connected together and moveably mounted to said base, said arms having mutually opening recesses to receive a sterile clamp in an open unlocked position with said recesses leading into said channel, one of said arms extending immediately adjacent said base and having at the opposite end thereof a conduit holder engageable with said port to hold said port in an immoveable straight position.

22. The device of claim 21 and further comprising a spike moveably mounted to said base and engageable with said port to be in fluid communication therewith as said conduit holder is engaged with said port and said sterile clamp holding means is subsequently moved to mount a sterile clamp onto said spike and port.

* * * * *